(12) United States Patent
Nanjo

(10) Patent No.: US 7,431,456 B2
(45) Date of Patent: Oct. 7, 2008

(54) FUNDUS CAMERA

(75) Inventor: Tsuguo Nanjo, Toyohashi (JP)

(73) Assignee: Nidek Co., Ltd. (JP)

( * ) Notice: Subject to any disclaimer, the term of this patent is extended or adjusted under 35 U.S.C. 154(b) by 0 days.

(21) Appl. No.: 11/648,133

(22) Filed: Dec. 29, 2006

(65) Prior Publication Data

US 2007/0146535 A1    Jun. 28, 2007

Related U.S. Application Data

(63) Continuation of application No. 08/960,825, filed on Oct. 30, 1997, now abandoned.

(51) Int. Cl.
*A61B 3/14* (2006.01)
*A61B 3/10* (2006.01)

(52) U.S. Cl. ..................... 351/206; 351/205

(58) Field of Classification Search ......... 351/200–205, 351/206, 207, 208, 245, 246; 348/78
See application file for complete search history.

(56) References Cited

U.S. PATENT DOCUMENTS

| | | | |
|---|---|---|---|
| 4,257,688 A * | 3/1981 | Matsumura | 351/206 |
| 4,436,388 A | 3/1984 | Takahashi et al. | 351/206 |
| 5,764,341 A * | 6/1998 | Fujieda et al. | 351/221 |
| 6,575,571 B2 * | 6/2003 | Shibata | 351/206 |

FOREIGN PATENT DOCUMENTS

| JP | 52-96533 A | 8/1977 |
|---|---|---|
| JP | 54-54494 A | 4/1979 |
| JP | 57-1322 A | 1/1982 |
| JP | 4-150830 A | 5/1992 |
| JP | 08-317905 A | 12/1996 |

OTHER PUBLICATIONS

Notice of Rejection, issued on Oct. 27, 2003, in corresponding Japanese Application No. Hei8-307181, pp. 1-3.
Notice of Rejection, issued on Feb. 27, 2004, in corresponding Japanese Application No. Hei8-307181, pp. 1-2.
Decision of Refusal, issued on Jun. 8, 2004, in corresponding Japanese Application No. Hei8-307181, pp. 1-2.
Notice of Rejection, issued on Jan. 6, 2004, in corresponding Japanese Application No. Hei9-61936, pp. 1-2.

* cited by examiner

*Primary Examiner*—Mohammed Hasan
(74) *Attorney, Agent, or Firm*—Rossi, Kimms & McDowell LLP

(57) ABSTRACT

A fundus camera includes a first illumination optical system for illuminating the fundus of the eye with infrared light, a second illumination optical system for illuminating the fundus of the eye with visible light used for photography that shares a part of the optical path with the first illumination optical system. A target projection optical system projects a target for focusing on the fundus. An observation optical system is provided with a focusing lens and a photographic element sensitive to infrared, thereby allowing the fundus to be observed. A display mechanism is provided to display an image obtained by the observational optical system. In addition, a mechanism is provided to move the target plate on the optical axis by interlocking the movement of the focusing lens with the observational optical system.

39 Claims, 5 Drawing Sheets

FUNDUS IMAGE

FUNDUS CAMERA

CROSS-REFERENCE TO RELATED APPLICATIONS

This application is a continuation application of U.S. patent application Ser. No. 08/960,825 filed on Oct. 30, 1997 now abandoned now on appeal.

BACKGROUND OF THE INVENTION

1. Field of the Invention

The present invention relates to a fundus camera for photographing a fundus of an eye to be examined, and more particularly to a focusing mechanism of the fundus camera suitable for focusing a fundus image illuminated by an infrared light.

2. Description of Related Art

The conventional fundus camera for photographing the fundus of the eye has been well-known as a non-mydriasis method of photographing the fundus image by using an infrared light as an illumination light for observation without using an additional medicine like a mydriatica. However, since the fundus image illuminated by the infrared light mainly seemed to be an image of blood vessel, the whole image was less contrasty and indistinct. As a result of this, the focusing was very difficult by only judging such a fundus image.

In order to solve this problem, by providing a target projecting optical system for projecting a target for focusing onto the fundus area, the target projecting optical system is coaxial with an optical axis of an illumination optical system for observation by an oblique mirror. Consequently, the apparatus for judging the suitability of focusing of the fundus image by observing a state of the target image projected on the fundus has been proposed. Since the target image for focusing is not necessary at photographing, it is structured that the target is not be projected by withdrawing the oblique mirror arranged on the optical axis of the illumination optical system.

However, it was necessary for the above-mentioned structured apparatus to provide a light source for projecting a target, a target plate, a relay lens, an oblique mirror and the like apart from the illumination optical system for observation. Also, since another mechanism of withdrawing the oblique mirror at photographing was needed, it resulted in a disadvantage that the whole structure was complicate. In view of this problem, it may be demerit for a handheld type of fundus camera to achieve compactness and lightening.

Further, if a focused range is enlarged, it may result another disadvantage that the difficulty of determining a focusing direction may cause unnecessary time for operating the apparatus.

SUMMARY OF THE INVENTION

An object of the present invention is to overcome problems described above and to provide a fundus camera, which is capable of projecting a target for focusing at the observation, and of removing a target projection at photographing with a simple structure.

Also, another object of the present invention provides the fundus camera for achieving a simple focusing.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, a fundus camera having a photographing optical system for photographing a fundus of an eye to be examined, the camera comprises a first illumination optical system for illuminating the fundus of the eye with using an infrared light, a second illumination optical system for illuminating the fundus of the eye with using a visible light for photography by sharing a part of an optical path with the first illumination optical system, a target plate for focusing which is disposed within the optical path shared by the first illumination optical system and the second illumination optical system, of which a target portion is formed by a filter having such wavelength characteristics that transmits a visible area and intercepts an infrared area, an observation optical system provided with a photographic element having sensitivity within the infrared area, for observing the fundus of the eye which is illuminated by the infrared light of the first illumination optical system and a target image of the target plate which is projected onto the fundus of the eye, displaying means for displaying an image obtained by the observation optical system; and moving means for moving the target plate on an optical axis by interlocking with a movement of a focusing lens of the observation optical system.

In another aspect of the present invention, the fundus camera further comprises travel-distance displaying means for displaying travel distances by the moving means.

In another aspect of the present invention, a fundus camera having illumination/target projection optical system and observation/photographing optical system, wherein the illumination/target projection optical system comprising at least an illumination light source for observation which emits an infrared light for illuminating a fundus of an eye to be examined, a flash light source for photography which emits a visible light for photographing the fundus of the eye, and a target plate which is disposed on an optical path for projecting a target for focusing onto the eye, the observation/photographing optical system comprising at least, a focusing lens which is disposed in a direction of optical axis so as to be movable, a mirror for wavelength selection which reflects either the infrared light or the visible light and transmits the other, a photographic CCD camera which senses the visible light delivered through the mirror, and photographs the fundus of the eye, and a CCD camera for observation which senses the infrared light delivered through the mirror, and observes the fundus of the eye, the target plate providing a target mark having characteristics of transmitting the visible light and intercepting the infrared light are formed on a base plate which transmits both of the infrared light and the visible light.

As describe above, and in accordance with the present invention, the apparatus enables a target projection for focusing upon observing, and enables a removal of the target projection upon photographing without providing such a complicate optical system or moving mechanism. Consequently, the compactness and lightening of the apparatus can be achieved.

Also, in accordance with the present invention, by providing a displaying mechanism that lens travel distances for focusing is converted into refractive power of the eye to be examined, the apparatus enables the operator to reduce irresolution caused by a screen which is out of focus, and enables an efficient alignment operation, especially the apparatus may be utilize for an unstable hand-held type apparatus and the like.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention.

In the drawings.

DETAILED DESCRIPTION OF THE PREFERRED EMBODIMENTS

Figure 1:
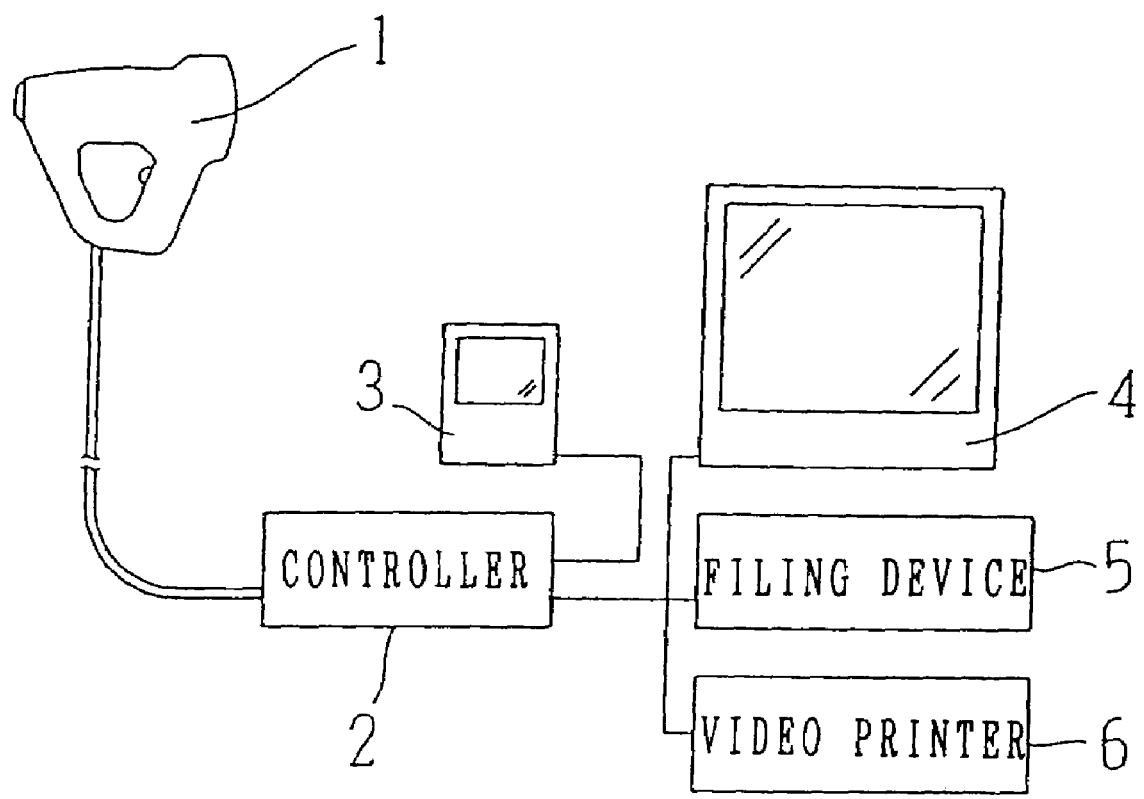
FIG. 1 is a view showing an outline structure of a fundus camera of the preferred embodiment of the present invention.

A detailed description of the present invention is provided below with reference to the accompanying drawing. FIG. 1 is a view showing an outline structure of a fundus camera of the preferred embodiment. The fundus camera of the preferred embodiment is generally structured by a photographing unit 1 storing an optical system and the like for observing and photographing into a body suitable for a hand-held operation, a controller 2 for controlling the photographing unit 1, an observation monitor 3, a display monitor 4, a filing device 5 and a video printer 6, and also each section is connected electrically.

Figure 2:
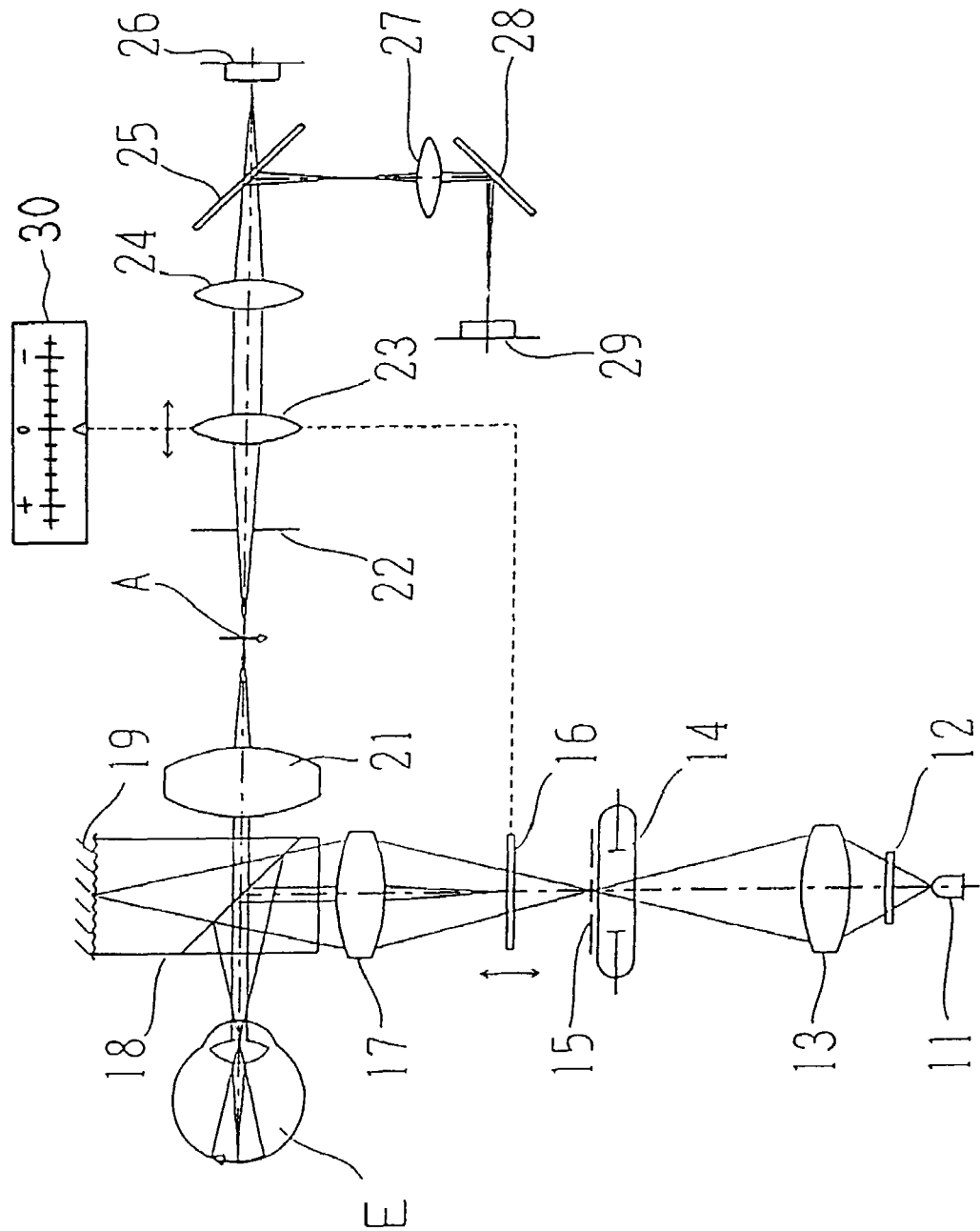
FIG. 2 is a view showing a detailed structure of optical system of the fundus camera of the preferred embodiment shown in FIG. 1.

FIG. 2 is a view showing a detailed structure of optical system of the fundus camera. The optical system will be described herein by dividing into the illumination/target projection optical system and the observation/photographing optical system separately.

(Illumination/Target Projection Optical System)

Figure 3:
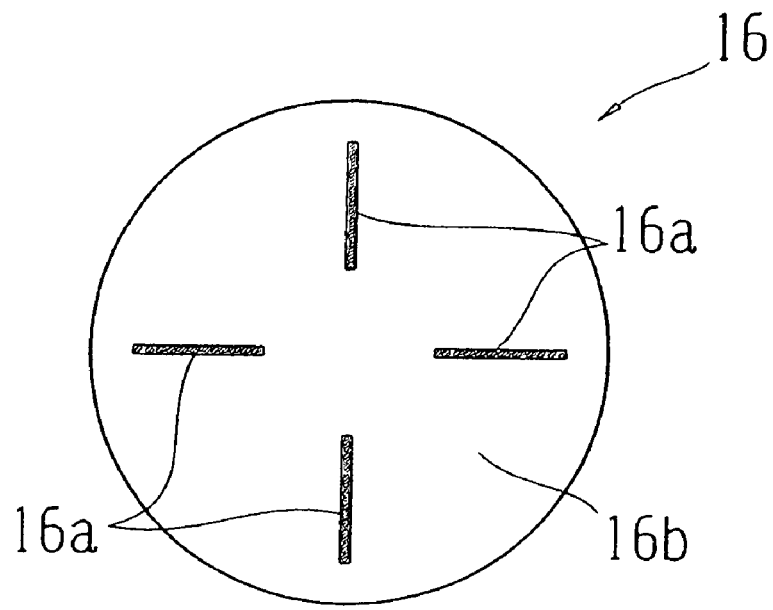
FIGS. 3(a) and 3(b) are views showing a target plate of the preferred embodiment shown in FIG. 2.
Figure 3:
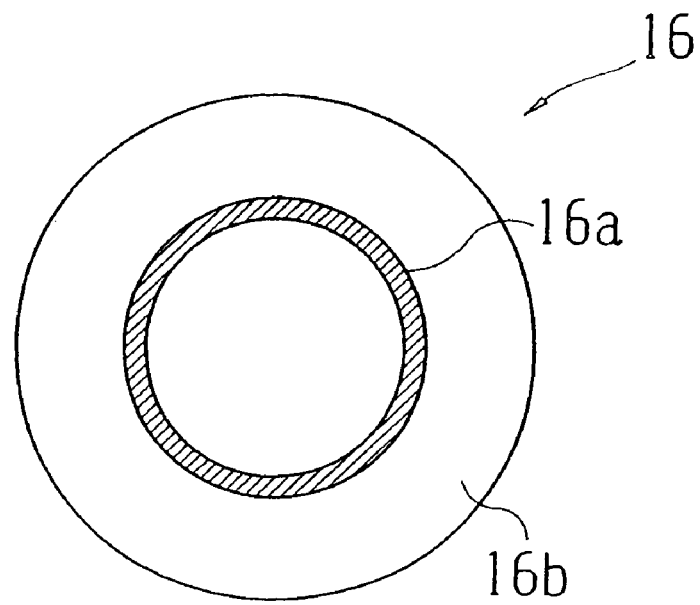

An infrared light emitting diode 11 is an illumination light source for observation, and is also used as a light source for projecting a target for focusing. Numeral 12 is a diffusion plate and 13 is a condenser lens. A flush light source 14 is a light source for photographing, and emits a visible luminous flux. Numeral 15 is a ring-slit which is a ring-shaped aperture diaphragm, and 16 is a target plate for projecting a target onto the fundus of the eye to be examined in order to focus a photographed part. As shown in FIGS. 3(a) and 3(b), the target plate 16 has a target mark 16a which is formed partially by a cross line (shown in FIG. 3(a)), a ring-shaped line (shown in FIG. 3(b)), or a combination shape of them and the like. The target mark 16a is formed by a coating (optical thin film) having a characteristic of wavelength for transmitting a visible area and for intersecting an infrared area. Using a cross-type of target is convenient, because some desired focusing points between the center and periphery can be easily confirmed at a position on a line. Also, it is convenient to use the ring-shaped target, because a whole focusing point may be confirmed on a line at the middle point of the image. Numeral 16b is a transmitting area surrounding the target mark 16a for transmitting both the visible area and the infrared area. Also, the target plate 16 is synchronized with a focusing lens 23 of the observation/projection optical system (which will be described hereinafter) so as to move in a direction of the optical axis (an arrow direction), thereby the focusing of the fundus can be achieved and arranged at a conjugate position.

Numeral 17 is a projection lens, and 18 is a beam splitter which makes the optical axis of the illumination/target projection optical system be coaxial with the optical axis of the observation/photographing optical system that will be described hereinafter. A black absorber 19 absorbs the illumination light without reflecting which attenuates and transmits through the beam splitter 18 so as to prevent a noise light unnecessary for use in the observation/photographing optical system from being incident. E is an eye to be examined.

The infrared light emitted from the infrared light emitting diode 11 is unified by the diffusion plate 12, and then the infrared light is focused by the condenser lens 13 so that the ring-slit 15 is completely illuminated. The target plate 16 is illuminated by the ring-shaped illumination light formed by the ring-slit 15. The luminous flux transmitted through the transmitting area 16b is incident on the beam splitter 18 passed though the projection lens 17, thereby the quantity of light is attenuated to approximate half so as to head for the eye E. The ring-slit 15 is conjugate to the adjacent to the pupil of the eye E when the photographing unit 1 is positioned at a predetermined working distance. Then, the luminous flux formed to be ring-shaped by the ring-slit 15 is diffused after forming the ring-slit image, so that the fundus of the same size as a field of vision which is photographed or of the larger size thereof to some extent is illuminated by an invisible infrared light. Since the target mark 16a on the target plate 16, the projection lens 17 and a crystalline lens of the eye E compose an image optical system for the fundus, the target mark 16a is projected onto the fundus as a shadow by the infrared light.

Further, the ring-slit 15 and the target plate 16 are illuminated by the light emitted from the flush light source 14. As the target mark 16a transmits the light of the visible area at this time, the visible luminous flux for photographing passes through without any obstruction caused by the target plate 16. After the luminous flux passes through the target plate 16, the fundus of the eye is illuminated by the luminous flux passed through the same optical path as the illumination luminous flux by the infrared light emitting diode 11.

(Observation/Photographing Optical System)

Numeral 21 is an objective lens for observation, and 22 is a photographing diaphragm which is arranged at the conjugate position adjacent to the pupil of the eye E in the same way of the ring-slit 15. A focusing lens 23 is adjustable by a lens moving mechanism (which is not illustrated) in the direction of the optical axis (an arrow direction) to adjust in accordance with a refractive power of the eye E. The focusing by the focusing lens 23 is allowable from a fundus photography as the basis for 0 D (for instance; +10 through −10 D) until a proximate photography for an anterior part or the like (for instance; +35 through −10 D). Numeral 30 is a refractive-power displaying meter for displaying travel distances which are converted into the refractive power of the eye E. Numeral 24 is an image forming lens, and a dichroic mirror 25 has a characteristic of reflecting the infrared light and transmitting the visible light. 26 is a CCD camera for photographing. 27 is a relay lens for extending the optical path, 28 is a mirror for reversing a mirror image, and 29 is an infrared CCD camera for observation.

The fundus of the eye E is illuminated by the infrared illumination light by the illumination/target projection optical system. The reflected light from the fundus by the above-mentioned illumination is emerged from the center of the optical axis that is not overlapped with the ring image by the ring-slit 15 adjacent to the pupil. The luminous flux emerged from the eye E is further attenuated to approximate half of the quantity of light by the beam splitter 18. After an inverted image is imaged at the point A by the objective lens 21, the luminous flux passes through the photographing diaphragm 22. Since the photographing diaphragm 22 is approximately conjugate with the pupil, a diameter of photographic luminous flux emerged from the pupil part of the eye E is determined by the photographing diaphragm 22 so as not to be overlapped with other ring image by the ring-slit 15. The position on the optical axis of the inverted image at the point A varies by the refractive power (diopter) of the eye E.

The luminous flux within the infrared area passed through the photographing diaphragm 22 passes through the focusing lens 23 and the image forming lens 24. After the luminous flux is reflected at the dichroic mirror 25, it is imaged on an photographic element of the CCD camera 29 for observation by the relay lens 27. A fundus image obtained by the CCD camera 29 for observation is displayed on the observation monitor 3. The focusing lens 23 is moved in order to correct the refractive power of the eye E and focus on the CCD camera 29 for observation corresponding to the movement of inverted image at the point A. The target plate 16 is simultaneously interlocked by this movement so as to project accurately on the fundus. The gap of travel distances by the interlock of the focusing lens 23 and the target plate 16 may be corrected by connecting a cam or the like.

In addition, since the travel distances of the focusing lens 23 which is moved for the purpose of correcting the refractive power of the eye E and focusing on the CCD camera 29 for observation may be converted into the refractive power of the eye E, the values which are converted into the refractive power may be displayed externally by the refractive-power displaying meter 30 (although it is convenient that the travel distances are converted into the refractive power, this method is not necessary). Also, as another method, since the target plate 16 is moved interlocked by the focusing lens 23, the travel distance of the target plate 16 may be converted into the refractive power of the eye E so as to display externally by the refractive-power displaying meter 30. Further, by the refractive-power display, the travel distances of the focusing lens 23 or the target plate 16 may be detected electrically, magnetically or optically, so that the refractive power may be obtained from the travel distance by a computer and displayed on the observation monitor 3 or the like.

Also, the visible reflected luminous flux from the fundus illuminated by the flush light source 14 for photographing passes through the objective lens 21, the photographing diaphragm 22, the focusing lens 23 and the image forming lens 24 so as to be incident on the dichroic mirror 25 in the same way of the reflected luminous flux from the fundus by the infrared light. Since the dichroic mirror 25 transmits the visible luminous flux, the visible reflected luminous flux from the fundus forms the fundus image on the photographic element of the photographic CCD camera 26 by the image forming lens 24. In this case, since the target plate 16 completely transmits the visible light of a photographic luminous flux, the target image of the target plate 16 is not formed within the visible area. Also, because the infrared luminous flux is reflected at the dichroic mirror 25, it may not be incident on the photographic CCD camera 26. As a result, the photographic CCD camera 26 can obtain the fundus image which is not effected by the target plate 16. The fundus image obtained by the photographic CCD camera 26 is displayed as a static image on the display monitor 4.

Figure 4:
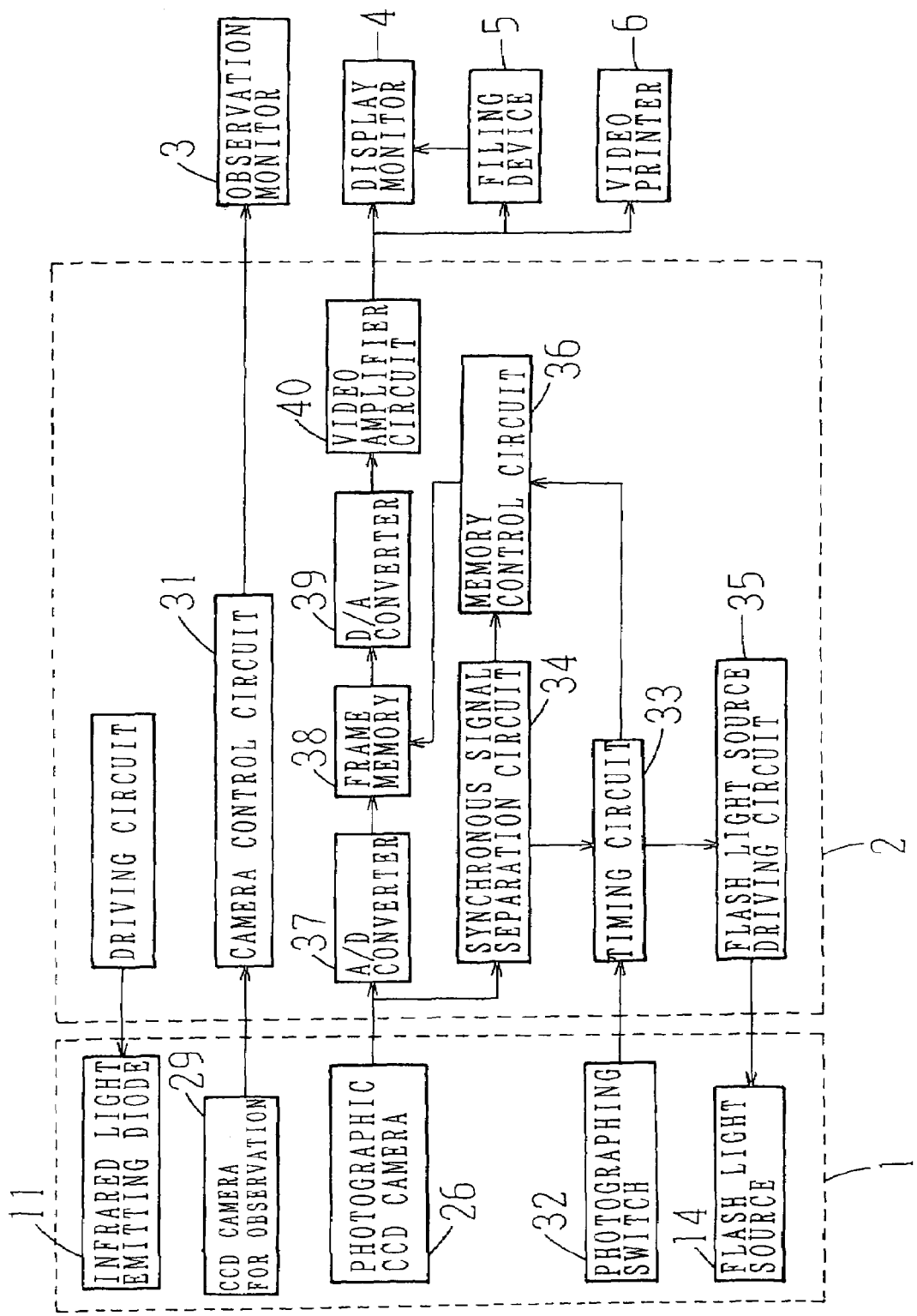
FIG. 4 is a block view of control system of the fundus camera of the preferred embodiment of the present invention.

In the fundus camera having the above-mentioned structure, the operation method will be described below with reference to a block diagram of the control system as shown in FIG. 4. The photographic condition may be desirable under the extent of approximate dim light, and also it may be desirable that the pupil of the eye E may be widely opened under the natural mydriasis. A driving circuit is driven by a switch arranged on the controller 2 (not illustrated) so as to turn on the infrared light emitting diode 11. The operator holds the body of the photographing unit 1 so that the eye E is illuminated in the slightly front side by bringing the photographing unit 1 close to the eye E. Since the luminous flux of the illumination for observation and the luminous flux of the target projection are the invisible infrared luminous flux, the eye E may be illuminated without any hardness.

The reflected luminous flux from the eye illuminated by the infrared luminous flux is caught by the CCD camera 29 for observation, so that the photographed image is displayed on the observation monitor 3 through a camera control circuit 31. Because the eye image observed on the observation monitor 3 is gradually illuminated from the front side, the anterior part of the eye E may be displayed at first. The operator brings the apparatus close to the position of working distance of the fundus camera with keeping his observation for the image. As a result of this, the pupil image becomes wider in the observation monitor 3 so that the fundus image may be displayed therein.

Figure 5:
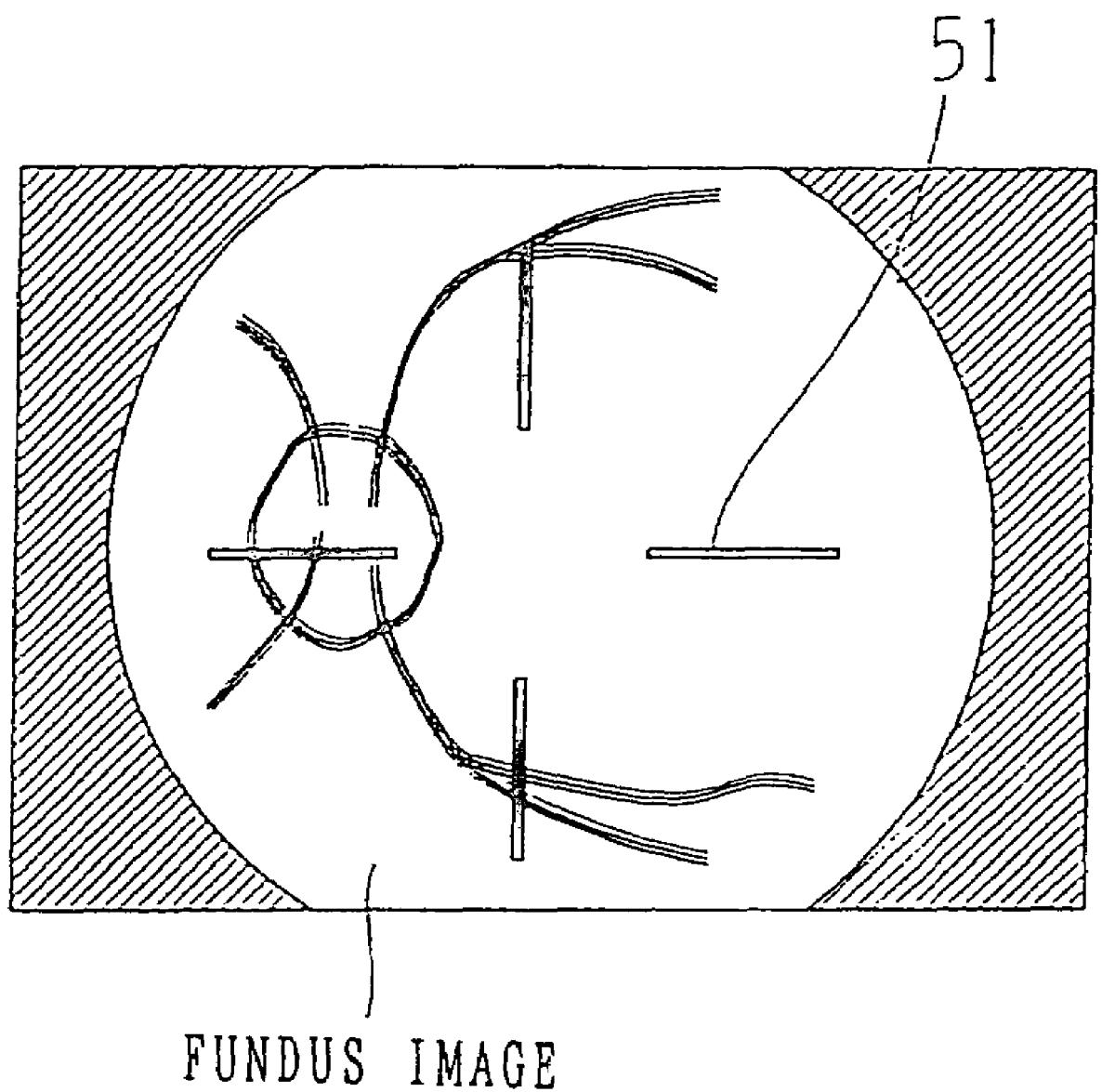
FIG. 5 is a view showing a sample of a fundus image displayed on an observation monitor.

FIG. 5 is a sample image displayed on the observation monitor 3 at this time (the target mark 16*a* formed by the cross line is utilized in FIG. 5). Under this condition, a target image 51 formed as a black shadow by the target mark 16*a* on the target plate 16 is displayed simultaneously with the fundus image on the observation monitor 3 for confirmation. The operator stops moving the photographing unit 1 when the pupil image of the eye becomes a desirable size (when the working distance is focused).

When the fundus is displayed on the observation monitor 3, the focusing lens 23 is moved in accordance with the refractive power of the eye E by the refractive-power displaying meter 30. As a result of this preparation, the efficient focusing may be achieved more than a method that the fundus is focused by moving the focusing lens 23 with observing a screen which is not focused yet. In this case, although it is necessary to know the refractive power of the eye E beforehand, because the refractive power of the eye is measured by an ophthalmic apparatus for measuring a refractive power in the objective way at the initial examination stage in the ophthalmic dispensary, its measured results may be available. On the other hand, if the refractive power of the eye E is not obtained yet, by returning the focusing lens 23 so as to change the basis of the refractive-power displaying meter to be 0 D, it is possible to focus plural fundus of the examinees approximately.

As shown in the above-mentioned process, when the focused fundus image is displayed on the observation monitor 3, the focusing of the fundus is adjusted accurately by moving the focusing lens 23. Because the fundus image illuminated by the infrared light mainly seems to be a red color image of blood vessel, the whole image may be less contrasty. Although it is not easy for persons who are not accustom to the observation to focus, the focusing can be achieved by observing the target image 51 which is displayed on the monitor 3. The target image 51 is displayed as a clear black shadow with contrast more than the fundus image which is displayed white on the black-and-white display of the observation monitor 3. Therefore, the operator may focus on the target image 51 so as to achieve the finest point. The target plate 16 is moved by interlocking with the movement of the focusing lens 23. When the focusing is completed, the focusing lens 23 makes the fundus (the inverted image at the point A) conjugate positions relative to the photographic surface of the photographic CCD camera 26 and the CCD camera 29 for observation respectively.

Further, since the travel distances of the focusing lens 23 in focus is displayed as the refractive power of the eye E on the refractive-power displaying meter 30, the details of the refractive-power displaying meter 30 may be standard in order to confirm the refractive power of the eye E.

In the next stage, the operator detailedly decides a desired photographed part of the fundus by swinging the photographing unit 1 at the center of the pupil with keeping his observation for the observation monitor 3. Another well-known method is also applicable to decide the photographed part by an external fixation light for leading a line of sight.

When the decision of the photographed part of the fundus is completed, a photographic switch 32 on the photographing unit 1 is pressed. A trigger signal is generated by pressing the photographic switch 32, so that the signal is inputted in a timing circuit 33 of the controller 2. The timing circuit 33 makes a synchronous signal from the photographic CCD camera 26 inputted through a synchronous signal separator circuit 34 synchronize, so that an operating signal is forwarded to a flash light source driving circuit 35 and a memory control circuit 36. The fundus image illuminated by a light emission from the flash light source 14 is caught by the photographic CCD camera 26. A picture signal caught by the photographic CCD camera 26 is digitized at an A/D converter, and then the picture image is synchronized with a signal from the memory control circuit 36 so as to be stored into a flame memory 38.

After the photo-image stored into the memory flame 38 is converted into an analog signal by a D/A converter, the signal is forwarded to the display monitor 4 through a video amplifier circuit 40 so that the photo-image may be displayed instantaneously.

Since the fundus image displayed on the display monitor 4 is within the visible area by a wavelength selection that a light from the flush light source 14 is selected by the dichroic mirror 25, the target mark 16a which only restricts in the infrared area may be not displayed thereon.

The operator confirms whether the displayed fundus image on the display monitor 4 is photographed fine or not. In case that the photo-image is not fine, some photographic conditions such an adjustment of the amount of the light for the flash light source 14 or the like are reset, and then the photographing should be performed once more in the same process.

In the case that the photo-image is stored, the data should be stored by operating the filing device 5. The photo-image data of the fundus image memorized and stored into the filing device 5 is retrievable, and the unnecessary photo-image may be deleted and edited. In addition, in the case that a printed image is necessary for pasting on medical records or the like, it can be printed out by operating the video printer 6.

Also, when the observation and photography for not only the fundus but also the anterior part or the like are performed, the refractive power with strong plus power is necessary for focusing on the proximate part. However, by moving the focusing lens 23 in a direction of plus refractive power with using the refractive-power displaying meter 30, the efficient focusing may be achieved.

The present invention may be embodied in other specific forms without departing from the spirit or essential characteristic thereof. For instance, although the observation monitor 3 is provided separately from the photographing unit 1 in the preferred embodiment, a miniature size of LCD (liquid crystal display) and the like may be also applied instead of the observation monitor 3 with photographing unit 1, so that the operation performance may be much better. Also, the observation monitor 3 and the display monitor 4 may provide with image switching means, thereby the observed image and photo-image can be displayed on the same monitor.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A fundus camera having a photographing optical system for photographing a fundus of an eye to be examined, the camera comprising:
    a first illumination optical system for illuminating the fundus of the eye with an infrared light;
    a second illumination optical system for illuminating the fundus of the eye with a visible light used for photography and which shares a part of an optical path with said first illuminating optical system;
    a target plate for focusing disposed within the optical path shared by said first illumination optical system and said second illumination optical system, of which a target is formed by a filter having such wavelength characteristics that it transmits a visible area and intercepts an infrared area;
    an observation optical system provided with a photographic element having sensitivity within the infrared area, for observing the fundus of the eye which is illuminated by the infrared light of said first illumination optical system and a target image of said target plate which is projected onto the fundus of the eye;
    displaying means for displaying an image obtained by said observational optical system; and
    moving means for moving said target plate on an optical axis by interlocking with a movement of a focusing lens of said observation optical system.

2. The fundus camera according to claim 1, wherein said photographing optical system shares a part of an optical path with said observation optical system, and the optical path shared by said photographing optical system and said observation optical system is separated by a mirror for wavelength selection which selects the infrared area and the visible area.

3. The fundus camera according to claim 1, wherein said first and second illuminating optical systems are coaxial with said photographing optical system and said observation optical system by a beam splitter.

4. The fundus camera according to claim 3, further comprising an absorber for absorbing an illumination luminous flux of said first and second illumination optical system which transmits said beam splitter without reflecting.

5. The fundus camera according to claim 1, wherein said target is a cross shape.

6. The fundus camera according to claim 1, wherein said target is a ring shape.

7. The fundus camera according to claim 1, wherein said target is a combination shape of the cross shape and the ring shape.

8. The fundus camera according to claim 1, wherein the camera comprises a body of handheld type.

9. The fundus camera according to claim 1, further comprising travel-distance displaying means for displaying travel distances by said moving means.

10. The fundus camera according to claim 9, wherein said travel-distance displaying means displays the travel distances by converting into refracting power.

11. The fundus camera according to claim 9, a focused limitation which is determined by a movement of the focusing lens by said moving means may cover from a proximate photography for an anterior part or the like until a photography for the fundus.

12. A fundus camera having an illumination/target projection optical system and an observation/photographing optical system, wherein said illumination/target projection optical system comprising at least:
an illumination light source for observation which emits an infrared light for illuminating a fundus of an eye to be examined;
a flash light source for photography which emits a visible light for photographing the fundus of the eye; and
a target plate which is disposed on an optical path for projecting a target for focusing onto the eye;
said observation/photographing optical system comprising at least:
a focusing lens which is disposed in a direction of an optical axis so as to be moveable;
a mirror for wavelength selection which reflects either the infrared light or the visible light and transmits the other;
a photographic CCD camera which senses the visible light delivered through said mirror, and photographs the fundus of the eye; and
a CCD camera for observation which senses the infrared light delivered through said mirror, and observes the fundus of the eye;
wherein said target plate providing a target mark having characteristics of transmitting the visible light and intercepting the infrared light are formed on a base plate which transmits both the infrared light and the visible light; and
wherein said target mark is formed on said base plate in a radial manner for four directions at equivalent interval of 90°.

13. The fundus camera according to claim 12, further comprising image displaying means for photograph for displaying the fundus image of the eye which is photographed by said photographic CCD camera.

14. The fundus camera according to claim 12, further comprising travel-distance displaying means for displaying movement distances of said focusing lens.

15. The fundus camera according to claim 14, wherein said travel-distance displaying means displaying the travel distances by converting into refractive power.

16. The fundus camera according to claim 14, a focused limitation which is determined by a movement of the focusing lens may cover from a proximate photography for an anterior part of the like until a photography for the fundus.

17. The fundus camera according to claim 12, wherein the camera comprises a body of hand held type.

18. The fundus camera according to claim 12, further comprising image displaying means for observation for displaying a fundus image of the eye which is observed by said CCD camera for observation.

19. A fundus camera having an illumination/target projection optical system and an observation/photographing optical system, wherein said illumination/target projection optical system comprising at least:
an illumination light source for observation which emits an infrared light for illuminating a fundus of an eve to be examined;
a flash light source for photography which emits a visible light for photographing the fundus of the eye; and
a target plate which is disposed on an optical path for projecting a target for focusing onto the eye;
said observation/photographing optical system comprising at least:
a focusing lens which is disposed in a direction of an optical axis so as to be moveable;
a mirror for wavelength selection which reflects either the infrared light or the visible light and transmits the other;
a photographic CCD camera which senses the visible light delivered through said mirror, and photographs the fundus of the eye; and
a CCD camera for observation which senses the infrared light delivered through said mirror, and observes the fundus of the eye;
wherein said target plate providing a target mark having characteristics of transmitting the visible light and intercepting the infrared light are formed on a base plate which transmits both the infrared light and the visible light; and
wherein said target mark is a ring shape.

20. The fundus camera according to claim 19, further comprising image displaying means for photograph for displaying the fundus image of the eye which is photographed by said photographic CCD camera.

21. The fundus camera according to claim 19, further comprising travel-distance displaying means for displaying movement distances of said focusing lens.

22. The fundus camera according to claim 21, wherein said travel-distance displaying means displaying the travel distances by converting into refractive power.

23. The fundus camera according to claim 19, a focused limitation which is determined by a movement of the focusing lens may cover from a proximate photography for an anterior part of the like until a photography for the fundus.

24. The fundus camera according to claim 19, further comprising image displaying means for observation for displaying a fundus image of the eye which is observed by said CCD camera for observation.

25. The fundus camera according to claim 19, wherein the camera comprises a body of handheld type.

26. A fundus camera having an illumination/target projection optical system and an observation/photographing optical system, wherein said illumination/target projection optical system comprising at least:
an illumination light source for observation which emits an infrared light for illuminating a fundus of an eye to be examined;
a flash light source for photography which emits a visible light for photographing the fundus of the eye; and
a target plate which is disposed on an optical path for projecting a target for focusing onto the eye;
said observation/photographing optical system comprising at least:

a focusing lens which is disposed in a direction of an optical axis so as to be moveable;

a mirror for wavelength selection which reflects either the infrared light or the visible light and transmits the other;

a photographic CCD camera which senses the visible light delivered through said mirror, and photographs the fundus of the eye; and a CCD camera for observation which senses the infrared light delivered through said mirror, and observes the fundus of the eye;

wherein said target plate providing a target mark having characteristics of transmitting the visible light and intercepting the infrared light are formed on a base plate which transmits both the infrared light and the visible light; and wherein said target mark is a combination shape of a cross shape and a ring shape.

27. The fundus camera according to claim 26, further comprising image displaying means for observation for displaying a fundus image of the eye which is observed by said CCD camera for observation.

28. The fundus camera according to claim 26, further comprising image displaying means for photograph for displaying the fundus image of the eye which is photographed by said photographic CCD camera.

29. The fundus camera according to claim 26, further comprising travel-distance displaying means for displaying movement distances of said focusing lens.

30. The fundus camera according to claim 29, wherein said travel-distance displaying means displaying the travel distances by converting into refractive power.

31. The fundus camera according to claim 29, a focused limitation which is determined by a movement of the focusing lens may cover from a proximate photography for an anterior part of the like until a photography for the fundus.

32. The fundus camera according to claim 26, wherein the camera comprises a body of handheld type.

33. A fundus camera having an illumination/target projection optical system and an observation/photographing optical system, wherein said illumination/target projection optical system comprising at least:

an illumination light source for observation which emits an infrared light for illuminating a fundus of an eye to be examined;

a flash light source for photography which emits a visible light for photographing the fundus of the eye; and a target plate which is disposed on an optical path for projecting a target for focusing onto the eye;

said observation/photographing optical system comprising at least:

a focusing lens which is disposed in a direction of an optical axis so as to be moveable;

a mirror for wavelength selection which reflects either the infrared light or the visible light and transmits the other;

a photographic CCD camera which senses the visible light delivered through said mirror, and photographs the fundus of the eye; and a CCD camera for observation which senses the infrared light delivered through said mirror, and observes the fundus of the eye;

wherein said target plate providing a target mark having characteristics of transmitting the visible light and intercepting the infrared light are formed on a base plate which transmits both the infrared light and the visible light; and wherein said target plate is disposed so as to be movable to an optical axis direction of said illumination/target projection optical system being synchronized with a movement of the focusing lens which is disposed in said observation/photographing optical system, and is disposed so as to be conjugate positional relationship with each other.

34. The fundus camera according to claim 33, further comprising image displaying means for photograph for displaying the fundus image of the eye which is photographed by said photographic CCD camera.

35. The fundus camera according to claim 33, further comprising travel-distance displaying means for displaying movement distances of said focusing lens.

36. The fundus camera according to claim 35, wherein said travel-distance displaying means displaying the travel distances by converting into refractive power.

37. The fundus camera according to claim 35, a focused limitation which is determined by a movement of the focusing lens may cover from a proximate photography for an anterior part of the like until a photography for the fundus.

38. The fundus camera according to claim 33, further comprising image displaying means for observation for displaying a fundus image of the eye which is observed by said CCD camera for observation.

39. The fundus camera according to claim 33, wherein the camera comprises a body of handheld type.

* * * * *